United States Patent [19]

Quang et al.

[11] Patent Number: 4,497,910

[45] Date of Patent: Feb. 5, 1985

[54] PROCESS FOR METHANE SYNTHESIS BY CATALYTIC REDUCTION OF CARBON MONOXIDE IN AQUEOUS PHASE

[75] Inventors: Dang V. Quang, Paris; André Sugier, Rueil Malmaison; Dominique Commereuc, Meudon; Yves Chauvin, Le Pecq, all of France

[73] Assignee: Institut Francais du Petrole, Rueil Malmaison, France

[21] Appl. No.: 402,673

[22] Filed: Jul. 28, 1982

[30] Foreign Application Priority Data

Jul. 28, 1981 [FR] France .................................. 81 14811
Mar. 25, 1982 [FR] France .................................. 82 05274

[51] Int. Cl.³ ................................................ C07C 1/04
[52] U.S. Cl. .................................... 518/700; 518/711; 518/715
[58] Field of Search ........................ 518/700, 711, 715

[56] References Cited

U.S. PATENT DOCUMENTS 3,930,812  1/1976  Harris et al. ........................ 518/711
4,171,320  10/1979  Vannice et al. ..................... 518/715
4,413,063  1/1983  Audibert et al. .................... 518/700

OTHER PUBLICATIONS

Tucci et al., "Hydrocarbon Processing", Apr. 1980, pp. 107–112.

Primary Examiner—Howard T. Mars
Attorney, Agent, or Firm—Millen & White

[57] ABSTRACT

Process for the catalytic synthesis of methane by reaction of carbon oxides with hydrogen in the presence of liquid water, wherein the catalyst is formed of a carrier consisting either of coal or charcoal, preferably of plant origin, or of alumina-silica, on which is deposited ruthenium, for example by impregnation with ruthenium acetylacetonate, said catalyst being preferably used as particles suspended in water.

12 Claims, No Drawings

PROCESS FOR METHANE SYNTHESIS BY CATALYTIC REDUCTION OF CARBON MONOXIDE IN AQUEOUS PHASE

BACKGROUND OF THE INVENTION

The present invention concerns a process for producing methane by reacting hydrogen with carbon oxides, particularly carbon monoxide.

It is known that one of the main difficulties in the catalytic synthesis of methane according to the equation:

$$3H_2 + CO \rightarrow CH_4 + H_2O$$

is a technological one and is related to the very high exothermicity of the reaction, so that for a mixture of $H_2$ and CO in stoichiometrical proportions, the temperature increase under adiabatic conditions is from 18° C. to 24° C. for each percent of conversion. The potential temperature increase for an assumed total conversion would thus be compared between 1800° and 2400° C.

Different techniques have been proposed to solve this problem:
1. The recycling of a substantial fraction of the gas in order to decrease the carbon oxide concentration; the heat evolved is then removed outside of the reactor,
2. The use of several reactors in series; the conversion rate in each reactor is limited by the selection of the operating conditions and the heat is removed between each reactor,
3. The use inside the reactor itself of a tubular system through which a cooling fluid is circulated.
4. A technique proposed in the U. S. Pat. No. 3,930,812, consists of passing liquid water through a methanation catalyst, simultaneously with the synthesis gas, the partial or total vaporization of said water making it possible to remove the reaction heat.

However, it is well known that most of the methanation catalysts, which are very active in gaseous phase or in the presence of a hydrocarbon liquid phase, generally quickly deactivate in the presence of liquid water. In the case of catalysts in bulk this effect is attributed to a sintering of the active phase. As concerns the catalysts formed of an active phase deposited and dispersed on an inorganic carrier, the deactivation may be attributed to the instability of the carriers commonly used in the presence of liquid water under the reaction conditions, i.e. at temperatures from 200° to 350° C. Thus, for example, a $\gamma$ alumina of high surface recrystallises to $\alpha$ alumina of low surface when it is heated for several days in liquid water.

SUMMARY OF THE INVENTION

The applicant has now found that it is possible to prepare methanation catalysts stable in liquid water under the methanation reaction conditions.

DETAILED DISCUSSION

According to the invention such catalysts are constituted of ruthenium or ruthenium compounds, deposited on coal of high specific surface or on aluminas stabilized by silica.

The coals or charcoals used according to the invention may be obtained by pyrolysis of various vegetable substances, such as wood, or from black coal, by means of various purification treatments, in particular for lowering the sulfur content. The coals obtained from coconut are preferred for this purpose and give the best results. The charcoals used according to the invention may also be obtained by synthesis, such as for example the carbon sieves. They may optionally be subjected to activation treatments such as washings with acid solutions, for example nitric acid. The specific surface of the coals or charcoals is high and may range from 200 to 1500 m² per gram.

They may be used as grains or powder having a particle size from 10 $\mu$m to 5 mm. They may optionally be crushed again after deposit of the ruthenium compound, in order to obtain the above defined size.

The aluminas stabilized by silica, as used according to the invention, comprise from 2 to 50% by weight of silica and preferably from 4 to 20% by weight. This silica may be added during the shaping, for example by bowl granulation or extrusion, as silica gel or colloidal silica, as silicates or aluminosilicates. After agglomeration, these carriers may be subjected to a treatment with water or with steam at a temperature between 100° and 300° C. before being thermally treated in neutral or oxidizing atmosphere at a temperature between 200° and 1100° C. and preferably between 400° and 900° C. The silica may also be added by impregnation of already shaped alumina with a solution, for example, of ethyl silicate, or with a solution of colloidal silica or any other kind of silica which may be solubilized in water or in any other solvent. The specific surface of the alumina carriers modified by silica is preferably from 30 to 400 m²/g. The carriers may be used as grains, balls or extrudates, for example from 0.1 to 10 mm of diameter. They may also be crushed in fine powder, of 10 $\mu$m to 1 mm.

The ruthenium content of the catalysts used according to the present invention is comprised between 0.01 and 5% by weight; contents from 0.5 to 3% will preferably be used. Ruthenium may be used alone or in combination with one or more other metals from group VIII of the periodical classification.

The ruthenium compounds which can be used according to the invention may be salts soluble in aqueous medium, such as ruthenium trichloride, ruthenium tribromide, or complexes also soluble in aqueous medium, such as potassium or ammonium hexachlororuthenate, rutheniumhexammine chloride, or a chloroammine complex, not well defined, known as ruthenium Red.

Another class of ruthenium compounds which can be used according to the invention consists of ruthenium complexes with at least one complexing agent. The complexing agents are organic compounds having at least two polar groups such as acid, ester, enol, ketone, alcohol, amide, imide or imine groups.

Certain of these complexes are soluble in aqueous medium, others in organic medium, for example in an alcohol, a hydrocarbon, a halogenated hydrocarbon, or mixtures thereof.

A preferred class is that of ruthenium acetylacetonates. Among other properties, they are soluble in hydrocarbon or halogenated, for example chlorinated, hydrocarbon medium.

The ruthenium deposit on the carrier is preferably effected by the conventional impregnation technique, whereby the pore volume of the carrier is filled with a solution containing the ruthenium compound.

Examples of solvents are water, alcohols, ethers, aliphatic or aromatic hydrocarbons, for example n-heptane, isooctane, a gasoline fraction, benzene or toluene. For the salts insoluble in aqueous medium, toluene is used preferably. The impregnation in aqueous medium may also be effected by the ionic exchange technique. This exchange may be controlled by adjusting the pH of the medium, for example by making use of hydrochloric or citric acid. Any other method of controlled impregnation known in the art may be used, for the purpose of obtaining a good ruthenium dispersion.

After impregnation with the ruthenium compound solution, the carrier is dried to evaporate the solvent and it is possible, if so desired, to subject it to a hydrogen treatment before use, for example at a temperature from 120° to 380° C. Previously, the carrier may be subjected to a roasting step in oxidizing medium, for example at 200° to 450° C.

In another embodiment of the process, the reactor consists of a vertical cylinder containing the catalyst and wherethrough passes upwardly the mixture of carbon oxides, hydrogen and liquid water in co-current. The reactor operates in fixed bed or expanded bed, depending on the circulation velocity of the aqueous phase. The catalyst used in this embodiment may be in the form of particles of 0.5 to 10 mm, preferably 0.5 to 3 mm.

In another embodiment, the heat generated by the reaction is removed partly by vaporization and partly by sensible heat of the cirulating liquid water. The discharged water may be recycled after passage through a cooling exchanger.

Other embodiments of the process may be used, such as described hereinafter:

In a first embodiment, the gaseous reactants, hydrogen and carbon oxides, as well as the aqueous liquid phase, circulate as a downward stream in the methanation reactor, the superficial velocity of the gaseous phase and of the liquid phase being each selected at least equal to 1.5 centimeter per second, preferably at least 3 cm/s. A preferred range of velocities is from 3 to 20 cm/s. By superficial velocity is meant the ratio of the volumic flow rate of liquid or gaseous phase, under the temperature and pressure conditions selected for the reaction, to the cross-sectional area of the reactor, considered as empty of catalyst.

The optimum superficial velocity depends, to a certain extent, on the size of the catalyst particles and on the physico-chemical properties of the liquid and of the gas. The catalyst particles have usefully an average diameter from 1 to 10 mm, preferably from 1.5 to 3 mm.

A good distribution of the liquid at the top of the reactor may be achieved by using a sprayer or a horizontal distribution plate provided with many perforations.

In this embodiment, the heat generated by the reaction is removed as sensible heat by the circulating liquid water; the water discharged may be recycled after passage through a cooling exchanger.

The reactor temperature is maintained between 200° and 330° C., preferably between 230° and 300° C., and the pressure between 3 and 26 MPa, preferably between 5.4 and 17 MPa.

In a second embodiment, the synthesized gas mixture consisting of hydrogen and carbon oxides, is bubbled through a catalyst suspension in liquid water, this suspension remaining in the reaction enclosure. The catalyst concentration by weight of said suspension is not critical. It is only limited by the viscosity under the reaction conditions, which must be sufficiently low to provide for a good diffusion of the synthesized mixture through the aqueous phase.

The reactor is equipped with a cooler, either integrated therein or arranged externally, so as to provide for the condensation of the formed steam and the return of the condensed water to the reactor. The cooler is so regulated as to maintain substantially constant the liquid level in the reactor.

The catalyst which can be used in this embodiment is in the form of particles having a size from 10 $\mu$m to 5 mm, preferably from 20 $\mu$m to 1 mm.

In this embodiment, the heat generated by the reaction is removed by the partial vaporization of the water present in the reactor.

The reactor temperature is maintained between 200° and 330° C., preferably between 230° and 300° C., and the pressure between 1.5 and 17.5 MPa, preferably between 3 and 12 MPa.

The third embodiment is similar to the second to the extent that the synthesized gas is also bubbled through a suspension of catalyst in liquid water, but it differs in that the catalyst suspension is circulated, for example by means of a pump, through an external cooling loop. The catalyst concentration by weight of this suspension must accordingly be reduced. It may be comprised between 1 and 40% and, preferably, between 5 and 30%.

An advantage of this embodiment is that it facilitates replacement, if necessary, of a part or the totality of the catalyst, by withdrawal of the used catalyst from the loop and introduction of an equivalent amount of fresh catalyst.

The catalyst which can be used in this embodiment is in the form of particles having a size from 10 $\mu$m to 5 mm, preferably from 20 $\mu$m to 1 mm.

This technique has been particularly developed by the applicant in a process of manufacturing cyclohexane: DUFAU et al., Chemical Engineering Progress, 60, 43–47 (1964), and CHA et al. Oil and Gas J., June 10, 1974, pages 64–65.

In this embodiment, the heat generated by the reaction is discharged partly by vaporization of water and partly as sensible heat of the liquid.

The reactor temperature is maintained between 200° and 330° C., preferably between 230° and 300° C., and the pressure from 1.5 to 26 MPa, preferably from 3 to 17 MPa.

In the above-described embodiments, the composition of the synthesis gas, expressed by the hydrogen/carbon monoxide molar ratio, may be from 0.5:1 to 6:1. Preferably, the operation is conducted with a ratio from 1:1 to 5:1, more particularly of about 3:1.

The hourly space velocity, expressed in volumes of gas mixture $H_2+CO$, under normal conditions, at the input, per catalyst volume and per hour (VVH), may vary from 1 to 25,000. Preferably, the operation is effected with values from 100 to 10,000.

The following examples illustrate the invention without limiting the scope thereof.

EXAMPLE 1

A reactor consisting of a stainless steel tube having an internal volume of 100 cm$^3$ is charged with 20 g of a catalyst consisting of ruthenium on alumina having a 6% by weight silica content. The catalyst has been prepared by impregnating the carrier with an aqeuous solution of ruthenium trichloride. The specific surface of the carrier, formed of 2 mm diameter balls, is 150 m$^2$/g and the ruthenium content is 1% by weight. The catalyst is pretreated in a hydrogen stream under atmospheric pressure at a temperature increasing from 120° to 380° C., over 4 hours, then the reactor is filled with water and pressurized.

From the bottom of the reactor, there is then introduced a synthesis gas whose H$_2$/CO composition is 3/1 by mole, at a flow rate of 50 l (NTP)/h as well as liquid water at a flow rate of 62 cm$^3$/h. The temperature is maintained at 250° C. and the pressure in the reactor at 4.3 MPa by means of a regulator placed at the reactor output.

The results are expressed by:
the conversion C in % mole, defined as:

$$C(\%) = \frac{CH_4 + \sum_{i=2}^{n} iC_iH_{2i+2} + CO_2}{CO \text{ (input)}} \times 100$$

the selectivity S$_{HC}$ to hydrocarbons, in % mole, defined as:

$$S_{HC}(\%) = \frac{CH_4 + \sum_{i=2}^{n} iC_iH_{2i+2}}{CH_4 + \sum_{i=2}^{n} iC_iH_{2i+2} + CO_2} \times 100$$

the methane fraction S$_{CH4}$ in % mole, defined as:

$$S_{CH4}(\%) = \frac{CH_4}{CH_4 + \sum_{i=2}^{n} iC_iH_{2i+1}} \times 100$$

The results obtained in a continuous run of 10 hours in the above conditions are:

C=99%

S$_{HC}$=95%

S$_{CH4}$=85%

The hydrocarbons other than methane consist essentially of ethane and propane.

EXAMPLE 2

In the same reactor and with the same catalyst as described in example 1, a ten hours second test is effected, following example 1.

The synthesis gas at the input has a composition H$_2$/CO: 1/1 by mole and is introduced at a flow rate of 50 l/h. Water is introduced at a rate of 68 cm$^3$/h. The temperature and pressure in the reactor are respectively 280° C. and 8.5 MPa.

The obtained results are the following:

C=75%

S$_{HC}$=96%

S$_{CH4}$=89%.

C, S$_{HC}$ and S$_{CH4}$ being defined as in example 1. The hydrocarbons other than methane are essentially ethane and propane, as well as traces of n-butane.

EXAMPLE 3

In the same reactor and with the same catalyst as described in example 1, and just following example 2, a ten hours third test is effected.

The synthesis gas, having a composition H$_2$/CO=3/1 by mole, is introduced at a rate of 80 l/h. Water is injected at a rate of 114 cm$^3$/h. The temperature and pressure in the reactor are respectively 300° C. and 9.4 MPa.

The obtained results, defined as in example 1, are as follows:

C=99.5%

S$_{HC}$=98%

S$_{CH4}$=96%

The only hydrocarbon found, besides methane, is ethane.

EXAMPLE 4

A catalyst has been prepared by impregnating with a ruthenium trichloride aqueous solution, a coconut charcoal having a specific surface of 1200 m$^2$/g, as grains of a 2 mm diameter. The so-prepared catalyst contains 1% by weight of ruthenium. 15 g of this catalyst are charged in the apparatus described in example 1. The catalyst is pretreated by a steam of hydrogen under atmospheric pressure at a temperature increasing from 120° to 380° C. over 4 hours, and then the reactor is filled with water.

There is then introduced, from the bottom of the reactor, a synthesis gas of molar composition H$_2$/CO=3/1 at a rate of 12 l (NTP)/h as well as liquid water at a rate of 15 cm$^3$/h. The temperature is maintained at 240° C. and the pressure at 4.5 MPa.

The results obtained in a 50 hours continuous run are as follows:

C=95%

S$_{HC}$=89.9%

S$_{CH4}$=75.2%

The conversion of CO remained stable during the whole test period. The hydrocarbons other than methane consist of ethane (5.6% by weight), propane (6.5% by weight) and butane (6.2% by weight).

EXAMPLE 5

15 g of the catalyst prepared as in example 1 are charged in the apparatus described in this example and pretreated by the same method. The reactor is then filled with water.

There is then introduced, from the bottom of the reactor, a synthesis gas of molar composition H$_2$/CO=3/1, at a flow rate of 12 l (NTP)/h, and liquid water at a rate of 15 cm$^3$/h. The temperature is maintained at 240° C. and the pressure at 4.5 MPa.

The results obtained over a 50 hours continuous run are as follows:

C=99%

S$_{HC}$=100%

$S_{CH_4} = 80.8\%$

The CO conversion remained stable during the whole test period. The hydrocarbons other than methane consist essentially of ethane and propane.

COMPARATIVE EXAMPLE 6

This example is given by way of comparison and forms no part of the invention. A ruthenium catalyst has been prepared by impregnation of γ alumina, of a specific surface of 250 m²/g, by means of a ruthenium trichloride aqueous solution. The ruthenium content is 1% by weight. 15 g of catalyst are charged into the reactor and pretreated as described in example 1. After having filled the reactor with water, there is introduced, from the bottom, 12 l (NTP)/h of a synthesis gas of composition $H_2/CO=3/1$, and 15 cm³/h of liquid water. The temperature is maintained at 240° C. and the pressure at 4.5 MPa.

During a 50 hours continuous run, the selectivities $S_{HC}$ and $S_{CH_4}$ remained respectively close to 90 and 80%. On the contrary the conversion C decreased continuously decreasing from an initial value of 98% to less than 55% at the end of the test. Besides, the specific surface of the alumina of the catalyst was no more than 11 m²/g.

This example shows the superiority of the catalysts according to the invention such as those of examples 4 and 5 compared to a catalyst of ruthenium on γ-alumina.

EXAMPLE 7

A reactor of 4 cm diameter and 1 m height is filled with a catalyst containing 3% of ruthenium on charcoal, prepared by impregnating a coconut charcoal having a specific surface of 1200 m²/g, as grains of 2 mm diameter, with a solution of ruthenium acetylacetonate in toluene. After evaporation of toluene under vacuum, the catalyst has been activated by passing a stream of hydrogen under atmospheric pressure at a temperature increasing from 120° to 380° C. for 4 hours.

At the top of the reactor there is introduced:
1. a synthesis gas having a molar composition hydrogen/carbon monoxide of 3/1, at a rate of 6 m³/h under normal conditions of temperature and pressure.
2. liquid water at a rate of 140 l/h measured at 20° C.

The reaction temperature is 245° C. and the pressure 7 MPa. In these conditions, the surface velocity of the gas is about 3.6 cm/s and that of the liquid about 3.8 cm/s. The liquid water is continuously recycled after passage through an external cooler.

The formed light hydrocarbons, consisting mainly of methane, are separated and analyzed after expansion to atmospheric pressure.

The obtained results are as follows:

$C = 50\%$ $S_{HC} = 95\%$ $S_{CH_4} = 88\%$.

EXAMPLE 8

In a reactor of the Grignard type having a useful volume of 250 cm³, equipped at its upper part with a cooler operating by water circulation, there is introduced 15 g of the catalyst prepared in example 1, after having crushed it to particles having an average size of 0.1 mm, and 100 cm³ of water. After having been purged with hydrogen, the reactor is heated to 280° C. and the pressure is adjusted to 7.5 MPa after introduction of a synthesis gas ($H_2/CO = 3/1$ by mole) at a rate of 50 l/h measured under normal conditions. The gas is introduced by means of a dip tube ending with a sintered material for its diffusion through the aqueous catalyst suspension. The produced hydrocarbons are recovered, after expansion, at the cooler output.

In these conditions, the obtained results are the following:

$C = 70\%$ $S_{HC} = 91\%$ $S_{CH_4} = 90\%$

EXAMPLE 9

In the reactor provided with an external circulation, as described in example 7, there is charged a suspension, in water, of the catalyst described in example 7 and crushed to particles of an average size equal to 100 μm, having a catalyst concentration of 2.5% by weight.

This suspension is circulated by means of a pump, upwardly through the reactor, and through the external cooling system.

The reactor is heated to 250° C. and the pressure is adjusted to 7 MPa. There is then introduced, from the bottom of the reactor, a synthesis gas ($H_2/CO=3/1$ by mole) at a rate of 1 m³/h measured under normal conditions.

The obtained results are the following:

$C = 75\%$ $S_{HC} = 93\%$ $S_{CH_4} = 91\%$

Substantially identical results are obtained when the direction of circulation of the suspension and of the synthesis gas in the reactor are reversed.

What is claimed is:

1. A process for the catalytic synthesis of methane, comprising the step of contacting a mixture of carbon oxides and hydrogen, in the presence of liquid water, with a catalyst comprising ruthenium deposited on a carrier formed of vegetable charcoal having a surface area of 200–1500 m²/g or alumina containing 2–50% by weight of silica.

2. A process according to claim 1, wherein said catalyst carrier is a vegetable charcoal.

3. A process according to claim 1, wherein said catalyst carrier is alumina, containing from 2 to 50% be weight of silica, and having a surface area of 30–400 m²/g.

4. A process according to claim 1, wherein ruthenium is deposited as ruthenium acetylacetonate.

5. A process according to claim 1, wherein the reactants and water circulate downwardly in a reaction zone containing a fixed bed of the catalyst, so that the superficial velocity of the gaseous phase and that of the liquid water are each 3–20 cm/s.

6. A process according to claim 1, wherein the catalyst is used as an aqueous suspension of particles whose size is from 20 μm to 1 mm, and wherein the reactor is equipped with a cooler for the automatic return of the condensate to the reactor, and is regulated so as to maintain constant the liquid water level in the reactor.

7. A process according to claim 1, wherein the catalyst is used as an aqueous suspension of particles of a size from 20 μm to 1 mm, and wherein said aqueous suspension, at a concentration between 5 and 30% by weight of catalyst, circulates upwardly through the reactor and through an external cooling loop.

8. A process according to claim 1, wherein the reaction temperature is from 200° to 330° C. and the pressure is from 1.5 to 26 MPa.

9. A process according to claim 8, wherein the hourly space velocity is 1 to 25,000 volumes of the mixture of carbon oxides and hydrogen per volume of the catalyst.

10. A process according to claim 8, wherein the hourly space velocity is 100 to 10,000 volumes of the mixture of carbon oxides and hydrogen per volume of the catalyst.

11. A process according to claim 2, wherein said vegetable charcoal is coconut charcoal.

12. A process according to claim 3, wherein said silica content is 4–20% by weight.

* * * * *